(12) United States Patent
Xiong et al.

(10) Patent No.: US 11,555,771 B2
(45) Date of Patent: Jan. 17, 2023

(54) METHOD AND DEVICE FOR SIMULTANEOUSLY MEASURING MASS CONCENTRATIONS OF PARTICULATES WITH DIFFERENT SIZES

(71) Applicant: Cubic Sensor and Instrument Co., Ltd, Wuhan (CN)

(72) Inventors: Youhui Xiong, Wuhan (CN); Zhiqiang Liu, Wuhan (CN); Tao He, Wuhan (CN); Wei Yang, Wuhan (CN)

(73) Assignee: CUBIC SENSOR AND INSTRUMENT CO., LTD, Wuhan (CN)

(*) Notice: Subject to any disclaimer, the term of this patent is extended or adjusted under 35 U.S.C. 154(b) by 120 days.

(21) Appl. No.: 17/138,951

(22) Filed: Dec. 31, 2020

(65) Prior Publication Data

US 2021/0123847 A1 Apr. 29, 2021

Related U.S. Application Data

(63) Continuation of application No. PCT/CN2018/098076, filed on Sep. 5, 2018.

(51) Int. Cl.
*G01N 15/02* (2006.01)
*G01N 15/06* (2006.01)
*G01N 33/00* (2006.01)

(52) U.S. Cl.
CPC ......... *G01N 15/0205* (2013.01); *G01N 15/06* (2013.01); *G01N 33/0027* (2013.01); *G01N 2015/0693* (2013.01)

(58) Field of Classification Search
CPC .............. G01N 15/0205; G01N 15/06; G01N 33/0027; G01N 2015/0693
See application file for complete search history.

(56) References Cited

U.S. PATENT DOCUMENTS

| 5,671,263 | A | * | 9/1997 | Ching-Ming | ......... G01T 1/1648 378/98.2 |
| 2003/0016357 | A1 | * | 1/2003 | Shofner | ............. G01N 15/0211 356/337 |
| 2011/0027825 | A1 | * | 2/2011 | Larsen | ............... G01N 15/1227 435/39 |
| 2016/0139024 | A1 | * | 5/2016 | Kim | .................. G01N 33/48785 435/287.1 |
| 2017/0248509 | A1 | * | 8/2017 | Godoy | ............... G01N 15/1456 |
| 2018/0231448 | A1 | * | 8/2018 | Moenkemoeller | .......................... G01N 15/0211 |

(Continued)

FOREIGN PATENT DOCUMENTS

| CN | 106383074 | A | * | 2/2017 |
| CN | 106442248 | A | | 2/2017 |

(Continued)

*Primary Examiner* — Dominic J Bologna
*Assistant Examiner* — Jarreas C Underwood
(74) *Attorney, Agent, or Firm* — Andrew C. Cheng

(57) ABSTRACT

The invention relates to a method and device for simultaneously measuring mass concentrations of particulates with different sizes. The method detects particulates within different size ranges in air based on laser scattering and can eliminate cross interference between the particulates within different size ranges. The device is simple in structure, can realize on-line simultaneous measurement of PM1.0, PM2.5 and PM10 with high measurement precision and low cost.

16 Claims, 4 Drawing Sheets

S1 — Calculate a correction coefficient of the number of small-diametersize particulates that are misjudged as large-diametersize particulates S2 — Correct a measured number of small-diametersize particulates or a measured number and mass concentration of large-diametersize particulates

(56) References Cited

U.S. PATENT DOCUMENTS

2019/0003951 A1* 1/2019 Sekimoto ............... G01N 21/64
2019/0317003 A1* 10/2019 Takasu .................. G01N 15/06

FOREIGN PATENT DOCUMENTS

| CN | 107132165 A | * | 9/2017 | ............ G01N 15/06 |
| CN | 107132165 A | | 9/2017 | |
| CN | 107607450 A | | 1/2018 | |
| CN | 107631963 A | | 1/2018 | |
| CN | 108303359 A | * | 7/2018 | ............ G01N 15/06 |
| CN | 108303359 A | | 7/2018 | |
| EP | 3214429 A1 | * | 9/2017 | ......... G01N 15/0205 |
| WO | WO-2017110435 A1 | * | 6/2017 | ......... G01N 15/1012 |

* cited by examiner

METHOD AND DEVICE FOR SIMULTANEOUSLY MEASURING MASS CONCENTRATIONS OF PARTICULATES WITH DIFFERENT SIZES

FIELD

The invention belongs to the technical field of air quality detection, and particularly relates to a method and device for simultaneously measuring mass concentrations of particulates with different sizes.

BACKGROUND

In recent years, the frequent occurrence of "haze" has raised close attention to particulates at home and abroad. Regarding particulate detection, *Ambient Air duality Standards* (GB 3095-2012) has been issued in China. Particulate monitoring methods internationally used mainly include weighing methods, β-ray absorption methods, tapered element oscillating microbalance and light scattering methods. The price of one set of particulate monitoring system is about 500,000 yuan, thousands of such monitoring systems have been established across the country, and the particulate pollution level in different regions of China is issued in real time on the website of the Ministry of Ecology and Environment of the People's Republic of China.

Under the circumstance that haze cannot be overcome in a short term, indoor air purifiers have become in high demand, and automotive air-conditioner purification systems are gradually becoming standard configurations of some automobiles. In addition, to form big data of particulate emission, meshed IoT monitoring has become an important means for controlling particulate emission and tracing particulates. Of all these means, the expensive monitoring systems adopted by the environmental departments cannot be popularized to a large scale. Thus, it is urgently needed to develop a high-precision and low-cost particulate sensor that can adapt to both indoor and outdoor application scenarios and can realize simultaneous multi-channel output.

China has become the biggest market of air purifiers around the world, and home-made high-precision and low-cost particulate sensors have been developed successively. Most of these sensors are designed based on laser scattering (adopting LEDs or laser infrared light sources), and the detection precision of low-cost indoor air quality (IA( ) sensors based on laser scattering has reached a high level. For example, Document U.S. Pat. No. 8,009,290B2 and Document CN105021501B can realize single-channel detection based on laser scattering. One sensor can only output the mass concentration of particulates with one size every time; and due to the cross interference between particulates with different sizes, multi-channel simultaneous measurement of different particulates cannot be realized (simultaneous output of PM1.0, PM2.5 and PM10), and only one of PM1.0, PM2.5 and PM10 can be output. At present, all international automobile manufacturers are required to measure PM1.0, PM2.5 and PM10 simultaneously, and as required by the Air Quality Association in Korea, indoor purifiers should simultaneously display PM1.0, PM2.5 and PM10. For example, Document CN103257095B adopts a two-stage cutter to simultaneously sample and measure PM2.5 and PM10; however, the cutter is complicated in structure, large in size and expensive, cannot realize on-line measurement, and is not beneficial to miniaturization or civil application and popularization. For another example, Document CN206223607U utilizes at least two photosensitive sensors to realize simultaneous measurement of PM2.5 and PM10; however, the cost is high, the size is large, the maintenance workload is large, and using is inconvenient.

During detection based on laser scattering, due to the non-uniform distribution of the light intensity near the laser focus of an air quality detection device, the light intensities scattered by particulates with the same size at different positions of the focus will be different, which may lead to a misjudgment of a photoelectric detector in the air quality detection device on the size of the particulates; and the cross interference between particulates with different sizes may result in inaccurate particulate concentration detection results. The distribution of particulates in air is very complicated, and the particulate size (referred to as size for short) of particulates in air generally ranges from 0.3 μm to 10 μm. Generally, particulates within a size range 0.3 μm<$d_1$≤1 μm are referred to as PM1.0, particulates within a size range 0.3 μm<$d_2$≤2.5 μm are referred to as PM2.5, and particulates within a size range 0.3 m<$d_3$≤10 μm are referred to as PM10. When the mass concentration of the particulates in air is detected, it is necessary to eliminate the cross interference between particulates with different sizes, and this is also a technical difficulty urgently to be overcome in the art.

SUMMARY

To solve the aforementioned problems, the invention provides a method and device for simultaneously measuring mass concentrations of particulates with different sizes. The method and device can eliminate the cross interference between particulates with different sizes and greatly improve the detection accuracy of the concentration of particulates.

In one aspect, the invention provides a method for simultaneously measuring mass concentrations of particulates with different sizes, comprising the following steps:

S1: calculating a correction coefficient of the number of small-size particulates that are misjudged as large-size particulates; and S2: correcting a measured number of small-size particulates or a measured number and mass concentration of large-size particulates according to the correction coefficient;

Wherein, the large-size particulates are particulates with sizes greater than a maximum size of the small-size particulates.

Furthermore, calculating the correction coefficient of the number of the small-size particulates that are misjudged as the large-size particulates in Step S1 comprises the following steps:

S11: collecting a measured air flow only containing small-size particulates, and detecting, by a multi-channel air quality detection device, the number of particulates with different sizes in the measured air flow to obtain the total number of the particulates with different sizes and the number of large-size particulates; and S12: dividing the number of the large-size particulates by the total number of the particulates with different sizes to obtain the correction coefficient of the number of the small-size particulates that are misjudged as the large-size particulates.

Furthermore, correcting the measured number of the small-size particulates according to the correction coefficient in Step S1 comprises the following steps:

S13: detecting, by the multi-channel air quality detection device, the number of particulates with different sizes in the measured air flow to obtain the total number of the particulates with different sizes and the number of large-size particulates;

S14: correcting the number of large-size particulates actually existing in the measured air flow according to the correction coefficient of the number of the small-size particulates that are misjudged as the large-size particulates obtained in S12, as well as the total number of the particulates with different sizes and the number of the large-size particulates obtained in S13, wherein the number of the large-size particulates actually existing in the measured air flow is calculated by the following formula:

(the number of the large-size particulates obtained in S13)−(the total number of the particulates with different sizes obtained in S13)*(the correct coefficient obtained in S12); and S15: obtaining the number of small-size particulates actually existing in the measured air flow according to the total number of the particulates with different sizes obtained in S13 and the number of the large-size particulates actually existing in the measured air flow obtained in S14, wherein the number of the small-size particulates actually existing in the measured air flow is calculated by the following formula:

(the total number of the particulates with different sizes obtained in S13)−(the number of the large-size particulates actually existing in the measured air flow obtained in S15).

Furthermore, the small-size particulates collected in Step S11 are generated by a standard particle generator, and/or are generated by burning a cigarette.

Furthermore, the total number of the particulates with different sizes is equal to the total number of the small-size particulates, and the number of the large-size particulates is the number of the misjudged small-size particulates of all the small-size particulates.

Furthermore, calculating the correction coefficient of the number of the small-size particulates that are misjudged as the large-size particulates in Step S1 comprises the following steps:

S21: collecting a measured air flow only containing small-size particulates, and detecting the number of particulates in the measured air flow to obtain a detection result; and S22: obtaining the proportion of small-size particulates that are misjudged as particulates with sizes greater than a maximum size of the small-size particulates and smaller than or equal to a maximum size of the large-size particulates according to the detection result, wherein the proportion is the correction coefficient of the number of the small-size particulates that are misjudged as the large-size particulates.

Furthermore, correcting the measured number and mass concentration of the large-size particulates according to the correction coefficient in Step S1 comprises the following steps:

S23: detecting, by a standard air quality detection device, the mass concentration of the small-size particulates in the measured air flow, and obtaining a first correlation coefficient between the number and mass concentration of the small-size particulates according to the number of the small-size particulates detected in Step S21;

S24: obtaining a second correlation coefficient between the number and mass concentration of the particulates with the sizes greater than the maximum size of the small-size particulates and smaller than or equal to the maximum size of the large-size particulates according to the maximum size of the small-size particulates, the first correlation coefficient and the maximum size of the large-size particulates; and S25: calibrating the multi-channel air quality detection device according to the correction coefficient of the number of the small-size particulates that are misjudged as the large-size particulates, the first correlation coefficient and the second correlation coefficient, and calculating and correcting the measured mass concentration of the large-size particulates to obtain a corrected mass concentration of the large-size particulates.

Furthermore, in Step S21, the number of the particulates in the measured air flow is detected through the following steps: detecting the measured air flow by a multi-channel particulate detection device, recording peak values of voltage pulses output by a photoelectric sensor in the multi-channel particulate detection device, taking a maximum peak value of a certain proportion of voltage pulses as a voltage threshold of particulates within a corresponding size range to obtain a voltage threshold of the small-size particulates and a voltage threshold of the large-size particulates, wherein particulates with pulse peak values smaller than or equal to the voltage threshold of the small-size particulates are judged as small-size particulates, and particulates with pulse peak values greater than the voltage threshold of the small-size particulates and smaller than or equal to the voltage threshold of the large-size particulates are judged as large-size particulates.

Furthermore, in Step S22, the correction coefficient of the number of the small-size particulates that are misjudged as the large-size particulates is calculated by the following formula:

(the number of the particulates with the sizes greater than the maximum size of the small-size particulates and smaller than or equal to the maximum size of the large-diameter particulates)/(the number of the small-size particulates).

Furthermore, in Step S23, the first correlation coefficient between the number and mass concentration of the small-size particulates is calculated by the following formula:

(the mass concentration of the small-size particulates in the measured air flow detected by the standard air quality detection device)/(the number of the small-size particulates)

Furthermore, in Step S24, the second correlation coefficient between the number and mass concentration of the particulates with the sizes greater than the maximum size of the small-size particulates and smaller than or equal to the maximum size of the large-size particulates is calculated by the following formula:

(the first correlation coefficient)*((the maximum size of the large-size particulates)/(the maximum size of the small-size particulates))$^3$.

Furthermore, in Step S25, the mass concentration of the large-size particulates is calculated by the following formula:

(the second correlation coefficient)*((the measured number of the large-size particulates)−(the number of the small-size particulates)*(the correction coefficient of the number of the small-size particulates that are misjudged as the large-size particulates))+(the calibrated mass concentration of the small-size particulates).

Furthermore, the small-size particulates in Step S21 are generated by a standard particle generator, and/or are generated by burning a cigarette.

Furthermore, in Step S11 and Step S21, the maximum size of the small-size particulates is 1 μm or 2.5 μm, and the maximum size of the large-size particulates is 2.5 μm or 10 μm.

Furthermore, the small-size particulates are PM1.0, and the large-size particulates are PM2.5 and/or PM10.

Furthermore, the small-size particulates are PM2.5, and the large-size particulates are PM10.

A device for simultaneously measuring mass concentrations of particulates with different sizes comprises a photoelectric sensor and a calibration module, wherein the calibration module carries out calibration through the method mentioned above.

The invention has the following beneficial effects: particulates within different size ranges in air are detected based on laser scattering, a multi-channel air quality detection device is used to detect the number of particulates within different size ranges in a cigarette and calculate a correction coefficient to correct the number of the particulates within different size ranges in air to eliminate the interference of the number of small-size particulates that are misjudged as large-size particulates on the coefficient relation between the number of the particulates within difference size ranges and an actual particulate concentration, and the multi-channel air quality detection device is calibrated. By adoption of the method and device, on-line simultaneous measurement of the mass concentration of particulates within different size ranges can be realized, the measurement precision is high, and the cost is low.

BRIEF DESCRIPTION OF THE DRAWINGS

FIG. 3 is a voltage chart of obtained by detecting particulates with sizes less than 1 μm;

DESCRIPTION OF THE EMBODIMENTS

The technical solution of the invention will be further specifically explained below in conjunction with embodiments and accompanying drawings.

As mentioned in the description of the related art, due to the non-uniform distribution of the light intensity near the laser focus of an air quality detection device, the light intensities scattered by particulates with the same size at different positions of the focus will be different, which may lead to a misjudgment of a photoelectric detector in the air quality detection device on the size of the particulates; and the cross interference between particulates with different sizes may result in inaccurate particulate concentration detection results.

Figure 1:
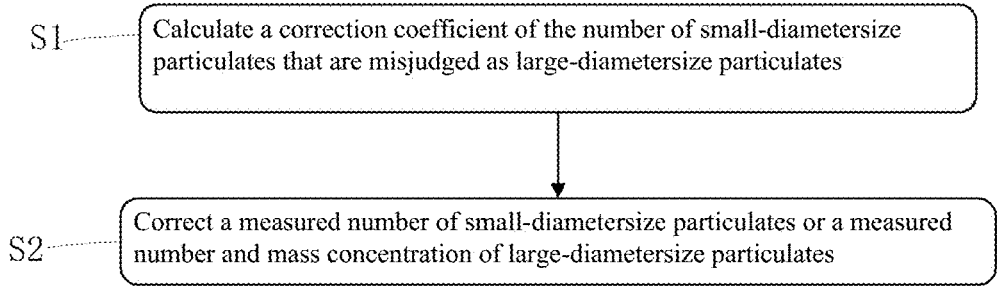
FIG. 1 is a general flow diagram of eliminating the cross interference of particulates within different size ranges of the invention.

Referring to FIG. 1 which illustrates a method for eliminating cross interference between particulates within different size ranges of the invention, the method comprises the following steps:

S1: a correction coefficient of the number of small-size particulates that are misjudged as large-size particulates is calculated; and S2: a measured number of small-size particulates or a measured number of mass concentration of large-size particulates are corrected according to the correction coefficient.

The large-size particulates are particulates with sizes greater than a maximum size of the small-size particulates.

Figure 2:
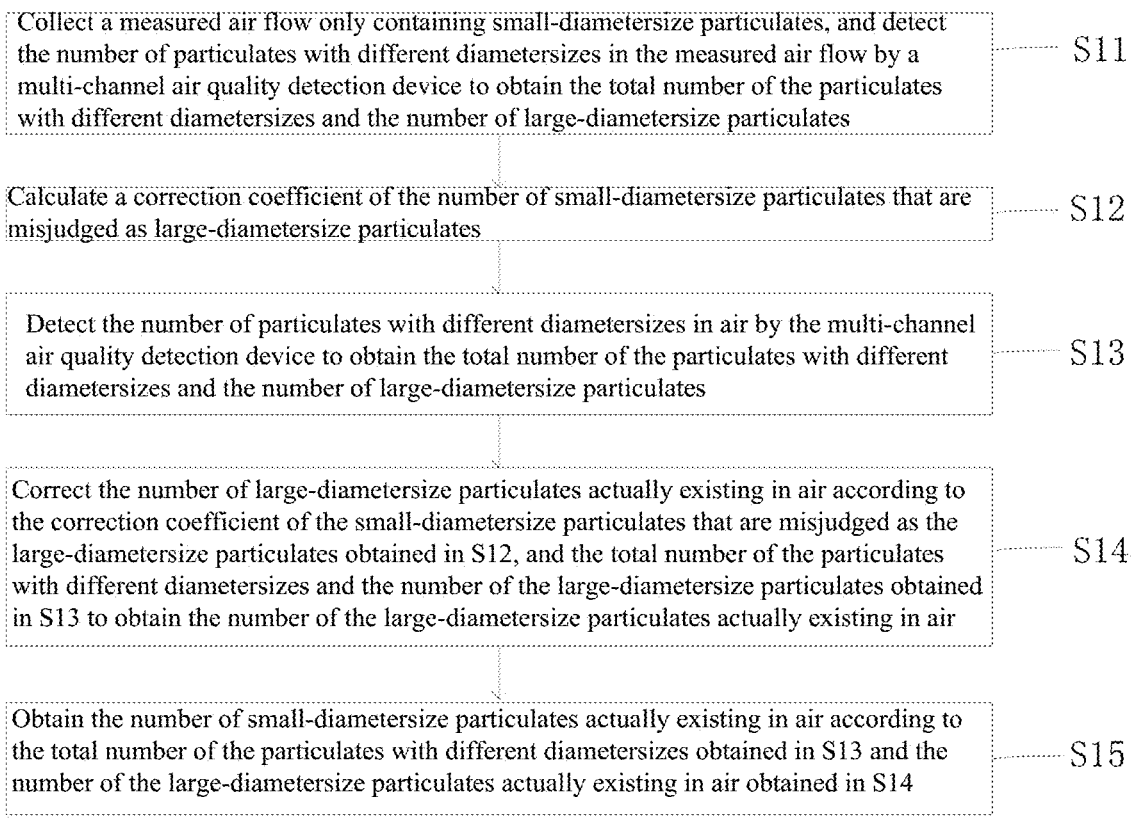
FIG. 2 is a flow diagram of eliminating the interference of large-size particulates on small-size particulates in Embodiment 1 of the invention.

Referring to FIG. 2, Embodiment 1 of the method for eliminating cross interference between particulates within different size ranges of the invention is illustrated. In Embodiment 1, the interference of small-size particulates that are misjudged as large-size particulates on the number of small-size particulates can be eliminated. The method will be explained below with reference to Embodiment 1.

Embodiment 1

As shown in FIG. 1 and FIG. 2:

S11: an air flow only containing small-size particulates was collected. In this embodiment, the small-size particulates are generated by a standard particle generator. If corresponding particulates cannot be generated due to the lack of the particle generator or other equipment, gas and particulates generated by a burning cigarette can be directly used as measured gas and measured particulates. The sizes of the particulates generated by the burning cigarette are basically smaller than or equal to 1 um, and the number of particulates within different size ranges in the measured gas generated by the burning cigarette is detected by means of a multi-channel air quality detection device, and is shown in Table 1-1:

TABLE 1-1

| Number of particulates within different size ranges in the cigarette | | | | | |
|---|---|---|---|---|---|
| Size distribution range | 0.3 μm < d3 ≤ 10 μm | | 1 μm < d4 ≤ 10 μm | | 2.5 μm < d5 ≤ 10 μm |
| Before correction | N | 10568 | $N_{large1}$ | 120 | $N_{large2}$ | 11 |
| After correction | N' | 10568 | $N_{large1}'$ | 0 | $N_{large2}'$ | 0 |

As shown in Table 1-1, according to the test results obtained by the multi-channel air quality detection device, the number N of particulates within the size range 0.3 μm<d3≤10 μm is 10568, the number $N_{large1}$ of particulates within the size range 1 μm<d4≤10 μm is 120, and the number $N_{large2}$ of particulates within the size range 2.5 μm<d5≤10 μm is 11. Under an ideal condition, the particulates generated by the standard particle generator or the cigarette should be within the small size range 0.3 μm<d1≤1 μm, so the total number of particulates within the size range 0.3 μm<d3≤10 μm detected by the multi-channel air quality detection device in this ideal condition should be equal to the number of particulates within the size range 0.3 μm<d1≤1 μm. However, the actual test results show that there are particulates within the size range 1 μm<d4≤10 μm and the size range 2.5 μm<d5≤10 μm, which indicate that part of all the particulates with the sizes greater than 1 μm and within the size range 0.3 μm<d3≤10 μm are misjudged.

S12: a correction coefficient $K_i$ of the number of small-size particulates that are misjudged as large-size particulates is calculated according to the above data:

$$K_i = \frac{N_{large}}{N}$$

Thus, the correction coefficient corresponding to the size range 1 µm≤d4≤10 µm is:

$$K_1 = \frac{N_{large1}}{N} = \frac{120}{10568} = 0.0114;$$

Thus, the correction coefficient corresponding to the size range 2.5 µm<d5≤10 µm is: $K_{2.5}$ $$K_{2.5} = \frac{N_{large2}}{N} \frac{11}{10568} = 0.001;$$

So, under the cigarette condition (the ideal condition), the total number of particulates within the size range 0.3 µm<d3≤10 µm is equal to the number of particulates within the size range 0.3 µm<d1≤1 µm, and the total number N of the particulates is not changed, that is, the total number of the particulates before correction is equal to the total number of the particulates before correction: N=N'=10568;

Under the cigarette condition, the multi-channel air quality detection device is used for detection and correction, and after correction, there is no particulate within the size range 1 µm<d4≤10 µm and the size range 2.5 µm<d5≤10 µm.

S13: the number of particulates within different size ranges in air is detected by the multi-channel air quality detection device and is shown in Table 1-2:

TABLE 1-2

Number of particulates within different size ranges in air

| Size distribution range | 0.3 µm < d3 ≤ 10 µm | | 1 µm < d4 ≤ 10 µm | | 2.5 µm < d5 ≤ 10 µm | |
|---|---|---|---|---|---|---|
| Before correction | n | 10037 | $n_{large1}$ | 216 | $n_{large2}$ | 17 |
| After correction | n' | 10037 | $n_{large1}'$ | 102 | $n_{large2}'$ | 7 |

As shown in Table 1-2, according to detection results obtained through the multi-channel air quality detection device, the total number n of particulates within the size range 0.3 µm<d3<10 µm is 10037, the number $n_{large1}$ of particulates within the size range 1 µm<d4≤10 µm is 216, and the number $n_{large2}$ of particulates within the size range 2.5 µm≤d5≤10 µm is 17;

S14: the number $n_{large}'$ of large-size particulates actually existing in air is corrected according to the correction coefficient $K_i$ determined under the cigarette condition in S12, n (n is the total number of particulates within different size ranges) obtained in 513, and $n_{large}$ obtained in S13:

$$N_{large}' = n_{large} - K_i \times n$$

Thus, the number $n_{large1}$ of the particulates within the size range 1 µm<d4≤10 µm is 216, and after being corrected, the number becomes: $n_{large1}' = n_{large1} - K_i \times n = 216 - 0.0114 \times 10037 = 102$;

Thus, the number $n_{large2}$ of the particulates within the size range 2.5 µm<d5≤10 µm is 17, and after being corrected, the number becomes: $n_{large2}' = n_{large2} K_{2.5} \times n = 17 - 0.001 \times 10037 = 7$;

After correction, the total number of the particulates is not changed: n=n';

S15: the number $n_{small}$ of small-size particulates actually existing in air is obtained according to n (n is the total number of particulates within different size ranges) obtained in S13 and the number $n_{large}'$ of the large-size particulates actually existing in air obtained after correction in S14, and after being corrected, the number $n_{small}$ of the small-size particulates within the small size range 0.3 µm<d1≤1 µm is:

$$N_{small} = n - n_{large1}' = 10377 - 102 = 10275.$$

Through the above steps, the influence of small-size particulates that are misjudged as large-size particulates on the number of small-size particulates and the number of large-size particulates is eliminated.

Referring to FIG. 1, FIG. 3, FIG. 4 and FIG. 5, Embodiment 2 of the method for eliminating cross interference between particulates within different size ranges of the invention is illustrated. In Embodiment 2, the interference of small-size particulates that are misjudged as large-size particulates on the number and mass concentration of large-size particulates can be eliminated. The method will be explained below with reference to Embodiment 2.

Embodiment 2

As shown in FIG. 1, FIG. 3, FIG. 4 and FIG. 5:

For example, in this embodiment, particulates within the size range 0.3 µm<d1≤1 µm are taken as first-size particulates (PM1.0), particulates within the size range 0.3 µm<d2≤2.5 µm are taken as second-size particulates (PM2.5), and a multi-channel air quality detection device is used to simultaneously detect the number and mass concentrations of the first-size particulates and the second-size particulates. The multi-channel air quality detection device can also be used to simultaneously detect the number and mass concentration of other different particulates.

Figure 3:
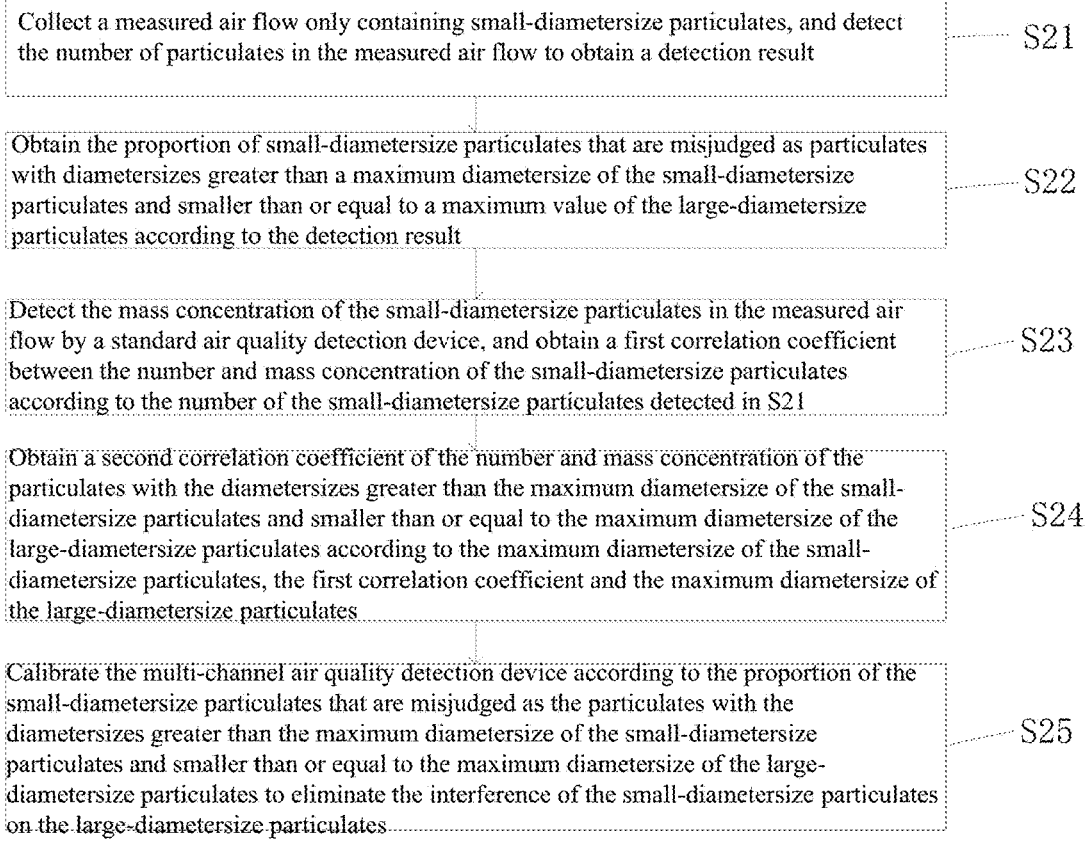
FIG. 3 is a flow diagram of eliminating the interference of small-size particulates on large-size particulates in Embodiment 2 of the invention.

As shown in FIG. 3, this embodiment provides a method for eliminating the interference of small-size particulates on large-size particulates, comprising the following steps:

S21: a measured air flow only containing the first-size particulates is collected and was detected by the multi-channel air quality detection device to obtain the number of particulates in the measured air flow;

By way of example, the multi-channel air quality detection device may be provided with different detection channels for simultaneously detecting the number of particulates of different types and with different sizes.

Specifically in Step S21, the measured air flow containing the first-size particulates are generated by a standard particle generator, and the measured air flow only contain the first-size particulates (such as 0.3 µm<d1≤1 µm) and does not contain other particulates with sizes greater than a maximum size of the first-size particulates, so that the number of first-size particulates that are misjudged as particulates with the sizes greater than the maximum size of the first-size particulates and smaller than or equal to a maximum size of the second-size particulates can be detected.

Due to the fact that a photoelectric sensor in the multi-channel air quality detection device may make a misjudgment (because the light intensity at or near the center of the laser focus is largest, the first-size particulates passing through the center or near the center of the laser focus may be misjudged as particulates with the sizes greater than the maximum size of the first-size particulates), not only the number $N_{small}$ of the first-size particulates but also the number $N_{large}$ of the first-size particulates that are misjudged as the particulates with the sizes greater than the maximum size of the first-size particulates and smaller than or equal to the maximum size of the second-size particulates (namely particulates within the size range 1 μm<d6≤2.5 μm) are obtained by detection.

Figure 4:
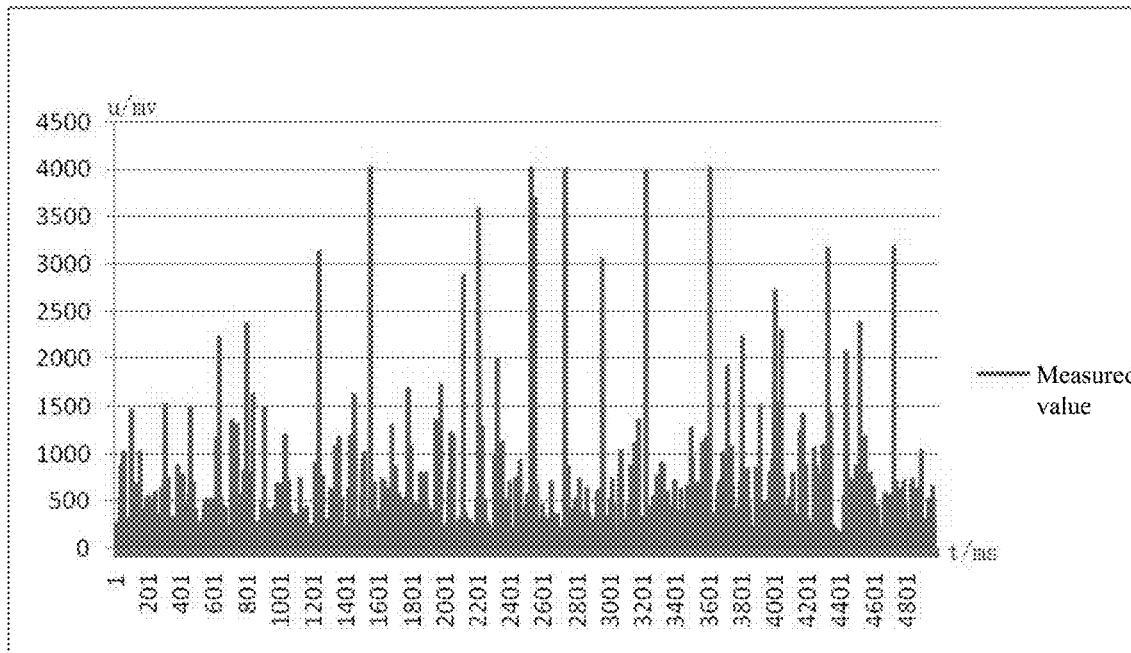

Furthermore, FIG. 4 illustrates voltage pulses continuously output by the photoelectric sensor of the multi-channel air quality detection device within a certain time when the measured air flow only containing the particulates within the size range 0.3 μm<d1≤1 μm (the first-size particulates) flow through the multi-channel air quality detection device. As can be seen from FIG. 4, peak values of the voltage pulses are 0~4000 mV, wherein each voltage pulse corresponds to one particulate, and theoretically, the larger the size of one particulate, the larger the peak value of the corresponding voltage pulse. To reduce errors, a maximum peak value of the voltage pulses of a certain proportion of samples is used as a voltage threshold, and the multi-channel air quality detection device can detect particulates with different sizes, so that particulates with different sizes have different corresponding voltage thresholds. Specifically, when the particulates within the size range 0.3 μm<d1≤1 μm pass through the multi-channel particulate detection device, the peak values of voltage pulses output by the photoelectric sensor of the multi-channel particulate detection device are recorded, and it is found that the maximum peak value of a certain number of samples, such as 98.7% of all the pulses, is 300 mV. On this basis, it can be known that the voltage threshold corresponding to the particulates within the size range 0.3 μm<d2≤2.5 μm is greater than or equal to 0 mV, and that the voltage threshold corresponding to the particulates within the size range 1 μm<d6≤2.5 μm is greater than or equal to 300 mV.

Figure 5:
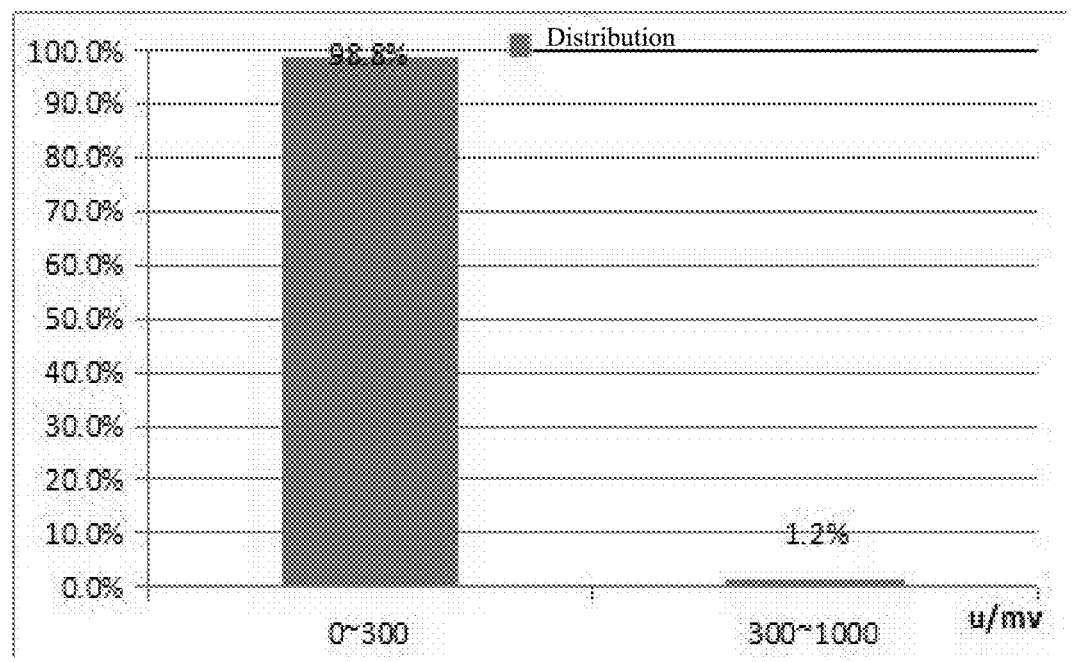
FIG. 5 is a voltage magnitude interval distribution chart of the voltage chart in FIG. 4.

Thus, the voltage pulses with the peak value greater than or equal to 0 mV in FIG. 5 are determined as particulates within the size range 0.3 μm<d2≤72.5 μm, and the voltage pulses with the peak value greater than or equal to 300 mV are determined as particulates within the size range 1 μm<d6≤2.5 μm, By multiple times of detection, data in FIG. 4 are recorded to obtain the number of particulates within four different size ranges, as shown in Table 2-1.

TABLE 2-1

| Number of particulates within four different size ranges | |
|---|---|
| $N_{total}$ (0.3 μm < d2 ≤ 2.5 μm) | $N_{large}$ (1 μm < d6 ≤ 2.5 μm) |
| 30361 | 350 |
| 21274 | 248 |
| 10688 | 120 |
| 5309 | 57 |

Four sets of data in Table 2-1a are obtained by collating data in Table 2-1.

TABLE 2-1a

| Four sets of collated data | | |
|---|---|---|
| $N_{total}$ (0.3 μm < d2 ≤ 2.5 μm) | $N_{large}$ (1 μm < d6 ≤ 2.5 μm) | $N_{small}$ (0.3 μm < d1 ≤ 1 μm) |
| 30361 | 350 | 30011 |
| 21274 | 248 | 21026 |

TABLE 2-1a-continued

| Four sets of collated data | | |
|---|---|---|
| $N_{total}$ (0.3 μm < d2 ≤ 2.5 μm) | $N_{large}$ (1 μm < d6 ≤ 2.5 μm) | $N_{small}$ (0.3 μm < d1 ≤ 1 μm) |
| 10688 | 120 | 10568 |
| 5309 | 57 | 5252 |

In addition, in this embodiment, an air flow generated by burning a cigarette can be directly used as the measured air flow. Because the size of particulates generated by the burning cigarette is basically smaller than or equal to 1 μm and is not greater than 1 μm, it can be determined that the air flow generated by the burning cigarette only contain the first-size particulates.

S22: the proportion of first-size particulates that are misjudged as particulates within the size range 1 μm<d6≤2.5 μm is obtained according to the number of particulates obtain in Step S11;

It is known by repeated verification that in the same air quality detection device, the proportion $$K_{mis} = \frac{N_{large}}{N_{total}} = \frac{N_{large}}{N_{small} + N_{large}}$$

of the first-size parameters (PM1.0) that are misjudged as the particulates within the size range 1 μm≤d6≤2.5 μm is constant, and that $N_{large}$ can almost be ignored with respect to $N_{small}$, $$\text{so } K_{mis} = \frac{N_{large}}{N_{total}} = \frac{N_{large}}{N_{small} + N_{large}}$$

is simplified into $$K_{mis} = \frac{N_{large}}{N_{total}} \approx \frac{N_{large}}{N_{small}}$$

By calculation according to data in Table 2-1a, $$K_{mis} = \frac{N_{large}}{N_{small}}$$

is about 1.15%.

Specifically, data in FIG. 4 is statistically calculated to obtain the statistical results in FIG. 5. As can be seen from FIG. 4, the proportion of particulates corresponding to a voltage peak from 0 to 300 mV was 98.8%, the proportion of particulates corresponding to a voltage peak greater than or equal to 300 mV is 1.2%, that is, the proportion of the first-size particulates (PM1.0) that are misjudged as the particulates within the size range 1 μm<d6≤2.5 μm is $K_{mis}$=1.2%, and is basically equal to $K_{mis}$ calculated according to Table 2-1a.

S23: the mass concentration $C_{small}$ of the first-size particulates in the measured air flow is detected by the standard air quality detection device, and a first correlation coefficient $K_{small}$ between the number and mass concentration of the first-size particulates is obtained according to the number $N_{small}$ of the first-size particulates obtained in Step S22;

Theoretically, in the same measurement environment, the number and mass concentration of particulates with the same size is in direct proportion. The mass concentration of the first-size particulates (PM1.0) in the measured air flow detected by the standard air quality detection device is $C_{small}$, and the coefficient between the number and mass concentration of the first-size particulates is denoted as the first correlation coefficient $K_{small}$, and $$K_{small} = \frac{C_{small}}{N_{small}}$$

In this embodiment, four sets of data about the mass concentration and number of the first-size particulates (PM1.0) obtained by multiple times of detection are shown in Table 2-2.

TABLE 2-2

Data about the mass concentration and number of the first-size particulates

| $N_{small}$ (0.3 μm < d1 ≤ 1 μm) | $C_{small}$ (0.3 < d1 ≤ 1 μm) |
|---|---|
| 30011 | 294 |
| 21026 | 207 |
| 10568 | 104 |
| 5252 | 52 |

The first correlation coefficient between the number and mass concentration of the first-size particulates (PM1.0) within the size range 0.3 μm<d1≤1 μm can be obtained by calculation according to the above calculation formula of the first correlation coefficient $K_{small}$, that is, $K_{small}$=0.0098.

S24: a second correlation coefficient $K_{large}$ between the number and mass concentration of the particulates within the size range 1 μm<d6≤2.5 μm is obtained according to the maximum size of the first-size particulates, the first correlation coefficient $K_{small}$ and the maximum size of the second-size particulates;

The correlation coefficients between the number and mass concentration of particulates with different sizes are different and are in direct proportion to the third power of the sizes of the particulates. In this embodiment, if the maximum size of the first-size particulates is denoted as $D_{small}$ and the maximum size of the second-size particulates is denoted as $D_{large}$, the second correlation coefficient between the number and mass concentration of the particulates within the size range 1 μm≤d6≤2.5 μm was $$K_{large} = K_{small} * \left(\frac{D_{large}}{D_{small}}\right)^3.$$

Data about the first correlation coefficient $K_{small}$ and the second correlation coefficient $K_{large}$ in Table 2-3 are obtained according to the calculation formula of $K_{small}$ and $K_{large}$.

TABLE 2-3

Data of four sets of first correlation coefficient $K_{small}$ and second correlation coefficient $K_{large}$

| $K_{small}$ (0.3 μm < d1 ≤ 1 μm) | $K_{large}$ (1 μm < d6 ≤ 2.5 μm) |
|---|---|
| 0.00980 | 0.1531 |
| 0.00984 | 0.1538 |
| 0.00984 | 0.1538 |
| 0.00990 | 0.1547 |

S25: the multi-channel air quality detection device is calibrated according to the proportion $K_{mis}$ of the first-size particulates that are misjudged as the particulates within the size range 1 μm<d6≤2.5 μm, the first correlation coefficient $K_{small}$ and the second correlation coefficient $K_{large}$ calculated in the above steps, so that the mass concentration of different particulates can be detected by the multi-channel air quality detection device.

The specific process of detecting particulates by the multi-channel air quality detection device is as follows: any one measured air flow is collected, for example, in this embodiment, an air flow containing PM1.0 and particulates within the size range 1 μm<d6≤2.5 μm is collected. The measured air flow is detected by the multi-channel air quality detection device, the number of the particulates within the size range 0.3 μm<d6≤2.5 μm is denoted as $_{total\ measured}$, the number of particulates with the size range 1 μm<d6≤2.5 μm (including the first-size particles (PM1.0) that are misjudged as particulates within the size range 1 μm<d6≤2.5 μm and particulates within the size range 1 μm<d6≤2.5 μm actually existing in the measured air flow) is denoted as $N_{large\ measured}$, and it can be known, by calculation, that the number of the particulates within the size range 0.3 μm<d1≤1 μm was $N_{small\ measured}=N_{total\ measured}-N_{large\ measured}$, and that the number of the first-size particulates that are misjudged as the particulates within the size range 1 μm<d6≤2.5 μm was $N_{mis}=K_{mis}*N_{small\ measured}$; after being corrected, the number of the particulates within the size range 1 μm<d6≤2.5 μm is $N_{large\ measured}'=N_{large\ measured}-N_{mis}=N_{large\ measured}-N_{small\ measured}*N_{mis}=N_{large\ measured}-(N_{total\ measured}-N_{large\ measured})*K_{mis}$.

After being corrected, the number of the particulates within the size range 0.3 μm<d1≤1.0 μm is $N_{small\ measured}'=N_{small\ measured}-N_{mis}=N_{small\ measured}+(N_{total\ measured}-N_{large\ measured})*K_{mis}$.

The mass concentration $C_{small\ calibrated}$ of the first-size particulates (PM1.0) is calculated according to the calibrated $K_{small}$ and $N_{small\ measured}$ obtained by calculation, and $C_{small\ calibrated}=K_{small}N_{small\ measured}'$; and the mass concentration $C_{large\ calibrated}$ of all particulates (PM2.5) within the size range 0.3 μm<d2≤2.5 μm is calculated according to $K_{large}$, $N_{large\ measured}$, $N_{total\ measured}$, $C_{small\ calibrated}$ and $K_{mis}$, and $C_{large\ calibrated}=K_{large}*N_{large\ measured}'+C_{small\ calibrated}=K_{large}*(N_{large\ measured}-N_{small\ measured}*K_{mis})+C_{small\ calibrated}$.

In this embodiment, the measured air flow containing PM1.0 (the first-size particulates within the size range 0.3 μm<d1≤1 μm) and the particulates within the size range 1 μm<d6≤2.5 μm is detected by the multi-channel air quality detection device to obtain particulate data in Table 2-4; the concentration of PM1.0 and PM2.5 is detected by a standard dust concentration detection device, and mass concentration data in Table 2-5 are obtained according to the calculation formula of $C_{large\ calibrated}$.

TABLE 2-4

Number of PM2.5 and the particulates within the size range 1 μm < d6 ≤ 2.5 μm obtained by detection

| $N_{total\ measured}$ (0.3 μm < d2 ≤ 2.5 μm) | $N_{large\ measured}$ (1 μm < d6 ≤ 2.5 μm) | $N_{small\ measured}$ (0.3 μm < d1 ≤ 1 μm) | $N_{mis}$ (1 μm < d6 ≤ 2.5 μm) | $N_{large\ measured}'$ (1 μm < d6 ≤ 2.5 μm) | $N_{large\ measured}'$ (0.3 μm < d1 ≤ 1 μm) |
|---|---|---|---|---|---|
| 30830 | 631 | 30199 | 347 | 284 | 30546 |
| 22121 | 438 | 21683 | 249 | 189 | 21932 |
| 10253 | 216 | 10037 | 115 | 101 | 10152 |
| 5193 | 97 | 5096 | 59 | 38 | 5155 |

TABLE 2-5

Mass concentrations detected by a standard instrument and obtained through the method in this embodiment

| Mass concentration detected by the standard instrument | | Mass concentration before interference is eliminated | | Mass concentration after interference is eliminated | |
|---|---|---|---|---|---|
| PM1.0 μg/m$^3$ | PM2.5 μg/m$^3$ | PM1.0 μg/m$^3$ | PM2.5 μg/m$^3$ | PM1.0 μg/m$^3$ | PM2.5 μg/m$^3$ |
| 295 | 340 | 296 | 393 | 299 | 342 |
| 210 | 241 | 212 | 279 | 215 | 244 |
| 100 | 114 | 98 | 131 | 99 | 114 |
| 52 | 57 | 50 | 65 | 51 | 57 |

As can be seen from the above Table, the precision of the mass concentration detected by the calibrated multi-channel dust concentration detection device is high, and the precision of the mass concentration of PM2.5 obtained after the interference of PM1.0 on PM2.5 is eliminated is higher than that of the directly measured mass concentration of PM2.5.

Through the above steps, the influence of the small-size particulates that are misjudged as large-size particulates on the mass concentration of the large-size particulates is eliminated.

The measured air flow containing PM1.0 and the particulates within the size range 1 μm<d6≤2.5 μm may be prepared from cigarette dust and A1 dust (ISO12103-1 A1 Ultra fine Test Dust).

Embodiment 3

As shown in FIG. 1, FIG. 3, FIG. 4 and FIG. 6:

For example, in this embodiment, particulates within the size range 0.3 μm<d1≤1 μm are taken as first-size particulates (PM1.0), particulates within the size range 0.3 μm<d2≤2.5 μm are taken as second-size particulates (PM2.5), particulates within the size range 0.3 μm<d3≤10 μm are taken as third-size particulates (PM10), and a multi-channel air quality detection device is used to simultaneously detect the number and mass concentration of the first-size particulates, the second-size particulates and the third-size particulates. The multi-channel air quality detection device can also be used to simultaneously detect the number and mass concentration of other different particulates.

Embodiment 3 differs from Embodiment 2 in the following aspects:

S21: due to the fact that a photoelectric sensor in the multi-channel air quality detection device may make a misjudgment, not only the number $N_{small}$ of the first-size particulates (PM1.0) but also the number $N_{large1}$ of first-size particulates (PM1.0) that are misjudged as particulates with sizes greater than a maximum size of the first-size particulates and smaller than or equal to a maximum size of the second-size particulates (that is, particulates within the size range 1 μm<d6≤2.5 μm) and the number $N_{large2}$ of first-size particulates that are misjudged as particulates with sizes greater than the maximum size of the second-size particulates and smaller than a maximum size of the third-size particulates (that is, particulates within the size range 2.5 μm<d5≤10 μm) are obtained.

Similar to Embodiment 2, detection results obtained by multiple times of detection are collated to obtain four sets of data about the number of particulates corresponding to different size ranges.

TABLE 3-1

Four sets of data about the number of particulates corresponding to different size ranges

| $N_{total}$ (0.3 μm < d3 ≤ 10 μm) | $N_{total1}$ (1 μm < d6 ≤ 10 μm) | $N_{large2}$ (2.5 μm < d5 ≤ 10 μm) | $N_{small}$ (0.3 μm < d1 ≤ 1 μm) | $N_{large1}$ (1 μm < d4 ≤ 2.5 μm) |
|---|---|---|---|---|
| 30391 | 380 | 30 | 30011 | 350 |
| 21295 | 269 | 21 | 21026 | 248 |
| 10699 | 131 | 11 | 10568 | 120 |
| 5314 | 62 | 5 | 5252 | 57 |

S22: it can be known, with reference to Embodiment 1, that the proportion of the first-size particulates (PM1.0) that are misjudged as the particulates within the size range 1 μm<d6≤2.5 μm is constant and is about 1.1%, and that the proportion of the first-size particulates (PM1.0) that are misjudged as the particulates within the size range 2.5 μm<d5≤10 μm is constant and is about 0.1%.

Figure 6:
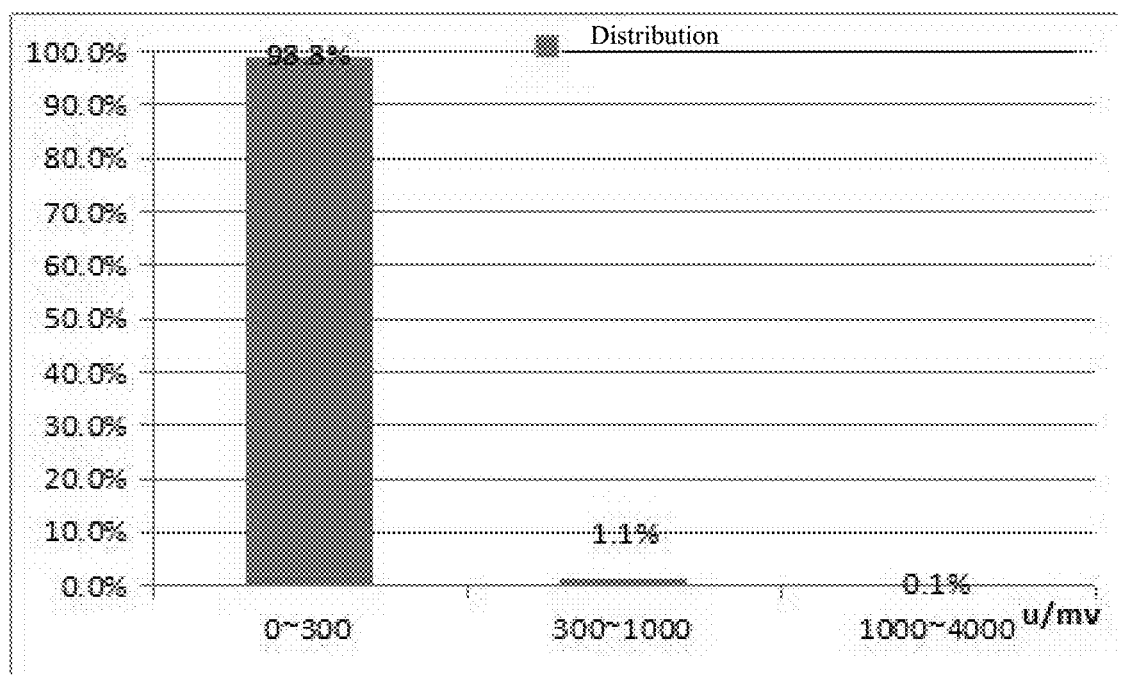
FIG. 6 is a more detailed voltage magnitude interval distribution chart of FIG. 4.

Specifically, data in FIG. 4 are recorded to obtain statistical results in FIG. 6. As can be seen from FIG. 6, voltages corresponding to 98.7% of the particulates are smaller than or equal to 300 mV, and voltages corresponding to 1.14% of the particulates are from 300 mV to 1000 mV, that is, the proportion of the first-size particulates that are misjudged as the particulates within the size range 1 μm<d6≤2.5 μm is $K_{mis1}$=1.14%; and voltages corresponding to 0.1% of the particulates are from 1000 mV to 4000 mV, that is, the proportion of the first-size particulates that are misjudged as the sizes within the size range 2.5 μm<d5≤10 μm is $K_{mis2}$=0.1%.

S23: the mass concentration of the first-size particulates in the measured air flow is detected by the standard air quality detection device, and a first correlation coefficient $K_{small}$ between the number and mass concentration of the first-size particulates is obtained according to the number of the first-size particulates detected in Step S11;

S24: a second correlation coefficient $K_{large1}$ between the number and mass concentration of the particulates within the size range 1 μm<d6≤2.5 μm and a third correlation coefficient $K_{large2}$ between the number and mass concentration of the particulates within the size range 2.5 μm<d5≤10 μm is obtained according to the maximum size of the first-size particulates, the first correlation coefficient $K_{small}$, the maximum size of the second-size particulates, and the maximum size of the third-size particulates;

Specifically, if the maximum size of the first-size particulates is denoted as $D_{small}$, the maximum size of the second-size particulates is denoted as $D_{large1}$ and the maximum size of the third-size particulates is denoted as $D_{large2}$, the second correlation coefficient between the number and mass concentration of the particulates within the size range 1 μm<d6≤2.5 μm is $$K_{large1} = K_{small} * \left(\frac{D_{large1}}{D_{small}}\right)^3,$$

the third correlation coefficient between the number and mass concentration of the particulates within the size range 2.5 μm<d5≤10 μm is $$K_{large2} = K_{small} * \left(\frac{D_{large2}}{D_{small}}\right)^3,$$

and data about the first correlation coefficient $K_{small}$, the second correlation coefficient $K_{large1}$ and the third correlation relation $K_{larg2}$ in Table 2-2 are obtained.

Table 3-2 Four sets of data about the first correlation coefficient $K_{small}$, the second correlation coefficient $K_{large1}$ and the third correlation relation $K_{large2}$:

TABLE 3-2

Data about correlation coefficients $K_{small}$, $K_{large1}$ and $K_{large2}$

| $K_{small}$ (0.3 μm < d1 ≤ 1 μm) | $K_{large1}$ (1μm < d6 ≤ 2.5 μm) | $K_{large2}$ (2.5 μm < d5 ≤ 10 μm) |
|---|---|---|
| 0.00980 | 0.1531 | 9.796 |
| 0.00984 | 0.1538 | 9.845 |
| 0.00984 | 0.1538 | 9.841 |
| 0.00990 | 0.1547 | 9.901 |

S25: the multi-channel air quality detection device is calibrated according to the proportion $K_{mis1}$ of the first-size particulates that are misjudged as the particulates within the size range 1 μm<d6≤2.5 μm, the proportion $K_{mis2}$ of the first-size particulates that are misjudged as the particulates within the size range 2.5 μm<d5≤10 μm, the first correlation coefficient $K_{small}$, the second correlation coefficient $K_{large1}$ and the third correlation coefficient $K_{large2}$ calculated in the above steps, so that the multi-channel air quality detection device can detect mass concentrations of multiple particulates.

The specific detection process is as follows: a measured air flow containing the first-size particulates, the particulates within the size range 1 μm<d6≤2.5 μm and the particulates within the size range 2.5 μm<d5≤10 μm is collected and is detected by the multi-channel air quality detection device; if the number of the particulates within the size range 0.3 μm<d≤10 μm obtained by detection is denoted as $N_{total\ measured}$ and the number of the particulates within the size range 1 μm<d≤10 μm obtained by detection is denoted as $N_{total1}$, it is known by calculation that the number of the first-size particulates (0.3 μm<d1≤1 μm) is $N_{small\ measured}=N_{total\ measured}-N_{total1}$; if the number of the particulates within the size range 1 μm<d6≤2.5 μm (including the first-size particulates that are misjudged as particulates within the size range 1 μm<d6≤2.5 μm and particulates within the size range 1 μm<d6≤2.5 μm actually existing in the measured air flow) is denoted as $N_{large\ measured1}$ and the number of the particulates within the size range 2.5 μm<d5≤1.0 μm (including the first-size particulates that are misjudged as the particulates within the size range 2.5 μm<d5≤10 μm and particulates within the size range 2.5 μm<d5≤10 μm actually existing in the measured air flow) is denoted as $N_{large\ measured2}$, it can be known, by calculation, that the number of the particulates within the size range 1 μm<d6≤2.5 μm (including the first-size particulates that are misjudged as the particulates within the size range 1 μm<d6≤2.5 μm and the particulates within the size range 1 μm<d6≤2.4 μm actually existing in the measured air flow) is $N_{large\ measured1}=N_{total1}-N_{large\ measured2}$;

The number of the first-size particulates that are misjudged as the particulates within the size range 1 μm<d6≤2.4 μm is $N_{mis1}=K_{mis1}*N_{small\ measured}$, and the number of the first-size particulates that are misjudged as the particulates within the size range 2.5 μm<d5≤10 μm is $N_{mis2}=K_{mis2}*N_{small\ measured}$; after being corrected, the number of the particulates within the size range 1 μm<d6≤2.5 μm is $N_{large\ measured1}'=N_{large\ measured1}-N_{mis1}=N_{large\ measured1}-N_{small\ measured}*K_{mis1}$, the number of the particulates within the size range 2.5 μm<d5≤10 μm is $M_{large\ measured2}'=N_{large\ measured2}=N_{mis2}=N_{large\ measured2}-N_{small\ measured}*K_{mis2}$, and the number of the particulates within the size range 0.3 μm<d1≤1 μm was $N_{small\ measured}'=N_{small\ measured}+N_{mis1}+N_{mis2}$.

The calibrated mass concentration $C_{small\ calibrated}$ of the first-size particulates (PM1.0) is calculated according to $K_{small}$ and $M_{small\ measured}$, wherein $C_{small\ calibrated}=K_{small} N_{small}$ measured; the mass concentration $C_{large\ calibrated1}$ of the second-size particulates (PM2.5) is calculated according to $K_{large1}$, $N_{large\ measured1}'$, $N_{small\ measured}$, $C_{small\ calibrated}$ and $K_{mis1}$, wherein $C_{large\ calibrated1}=K_{large1}*(N_{large\ measured1}-N_{small\ measured}*K_{mis})+C_{small\ calibrated}$.

Similarly, the mass concentration of the third-size particulates (PM10) is calculated according to $K_{large2}$, $N_{large\ measured2}'$, $N_{small\ measured}$, $C_{small\ calibrated}$ and $K_{mis2}$, wherein $C_{large\ calibrated2}=K_{large2}*(N_{large\ measured2}-N_{small\ measured}*K_{mis2})+C_{large\ calibrated1}$.

In this embodiment, detection data obtained by detecting the measured air flow containing PM1.0 (namely the first-size particulates within the size range d1≤1 μm), the particulates within the size range 1 μm<d6≤2.5 μm and the particulates within the size range 2.5 μm<d5≤10 μm by the multi-channel air quality detection device are collated to obtain the number of particulates within different size ranges, as shown in Table 3-3; the concentration of PM1.0, PM2.5 and PM10 in the same air flow are detected by a standard dust concentration detection device to obtain the mass concentration data shown in Table 3-4.

TABLE 3-3

Number of particulates within different size ranges

| $N_{small\ measured}$ (0.3 μm < d1 ≤ 1 μm) | $N_{large\ measured1}$ (1 μm < d6 ≤ 2.5 μm) | $N_{mis\ 1}$ (1 μm < d6 ≤ 2.5 μm) | $N_{large\ measured1}'$ (1 μm < d6 ≤ 2.5 μm) | $N_{large\ measured2}$ (2.5 μm < d5 ≤ 10 μm) | $N_{mis2}$ (2.5 μm < d5 ≤ 10 μm) | $N_{large\ measured2}'$ (2.5 μm < d5 ≤ 10 μm) |
|---|---|---|---|---|---|---|
| 30199 | 631 | 352 | 279 | 47 | 30 | 17 |
| 21683 | 438 | 256 | 182 | 34 | 22 | 12 |
| 10037 | 216 | 114 | 102 | 17 | 10 | 7 |
| 5096 | 97 | 55 | 42 | 9 | 5 | 4 |

TABLE 3-4

Mass concentrations of PM1.0, PM2.5 and PM10 detected by a standard instrument and obtained through the method in this embodiment

| Mass concentration detected by the standard instrument | | | Mass concentration before interference is eliminated | | | Mass concentration after interference is eliminated | | |
|---|---|---|---|---|---|---|---|---|
| PM1.0 μg/m$^3$ | PM2.5 μg/m$^3$ | PM10 μg/m$^3$ | PM1.0 μg/m$^3$ | PM2.5 μg/m$^3$ | PM10 μg/m$^3$ | PM1.0 μg/m$^3$ | PM2.5 μg/m$^3$ | PM10 μg/m$^3$ |
| 295 | 340 | 516 | 296 | 392 | 853 | 296 | 339 | 503 |
| 210 | 241 | 363 | 213 | 281 | 616 | 213 | 242 | 363 |
| 100 | 114 | 178 | 99 | 132 | 299 | 99 | 114 | 179 |
| 52 | 57 | 92 | 50 | 65 | 155 | 50 | 57 | 98 |

As can be known from the above table, the precision of the mass concentration of PM1.0 detected by the calibrated multi-channel dust concentration detection device is high, the precision of the mass concentration of PM2.5 obtained after the interference of PM1.0 on PM2.5 is eliminated is higher than that of the directly measured mass concentration of PM2.5, and the precision of the mass concentration of PM10 obtained after the interference of PM1.0 on PM10 is eliminated is higher than that of the directly measured mass concentration of PM10.

The interference of high-concentration PM1.0 (first-size particulates) on the mass concentration of low-concentration PM2.5 (the second-size particulates) and the mass concentration of low-concentration PM10 (the third-size particulates) is eliminated from detection results, so that this solution can greatly improve the precision of dust concentration detection results.

Embodiment 4

Figure 7:
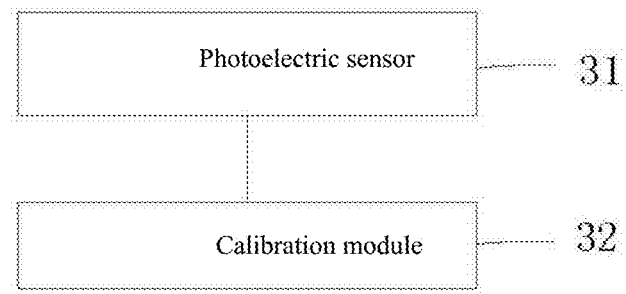
FIG. 7 is a block diagram of a device for high-precision simultaneous measurement of mass concentrations of particulates with different sizes.

Referring to FIG. 7, a device for simultaneously measuring mass concentrations of particulates with different sizes comprises a photoelectric sensor 31 and a calibration module 32, wherein the calibration module 32 carries out calibration through the method in any one of Embodiment 1 and Embodiment 2.

The specific embodiments described in this description are merely for illustrating the spirit of the invention. Those skilled in the art can make different modifications, supplements or similar equivalents to these specific embodiments without departing from the spirit of the invention or going beyond the scope defined by the appended claims.

The above embodiments and the characteristics in these embodiments can be mutually combined without causing any conflict.

The above embodiments are merely preferred ones of the invention, and are not intended to limit the invention. Any modifications, equivalent substitutions and improvements made on the basis of the spirit and principle of the invention should also fall within the protection scope of the invention.

What is claimed is:

1. A method for simultaneously measuring mass concentrations of particulates with different sizes, comprising the following steps:
   S1: calculating a correction coefficient of the number of small-size particulates that are misjudged as large-size particulates; and
   S2: correcting a measured number of small-size particulates or a measured number and mass concentration of large-size particulates according to the correction coefficient;
   wherein the large-size particulates are particulates with sizes greater than a maximum size of the small-size particulates; and
   wherein calculating the correction coefficient of the number of the small-size particulates that are misjudged as the large-size particulates in Step S1 comprises the following steps:
   S11: collecting a measured air flow only containing small-size particulates, and detecting, by a multi-channel air quality detection device, the number of particulates with different sizes in the measured air flow to obtain the total number of the particulates with different sizes and the number of large-size particulates; and
   S12: dividing the number of the large-size particulates by the total number of the particulates with different sizes to obtain the correction coefficient of the number of the small-size particulates that are misjudged as the large-size particulates.

2. The method according to claim 1, wherein correcting the measured number of the small-size particulates according to the correction coefficient in Step S2 comprises the following steps:
   S13: detecting, by the multi-channel air quality detection device, the number of particulates with different sizes in the measured air flow to obtain the total number of the particulates with different sizes and the number of large-size particulates;
   S14: correcting the number of large-size particulates actually existing in the measured air flow according to the correction coefficient of the number of the small-size particulates that are misjudged as the large-size particulates obtained in S12, as well as the total number of the particulates with different sizes and the number of the large-size particulates obtained in S13, wherein the number of the large-size particulates actually existing in the measured air flow is calculated by the following formula:

(the number of the large-size particulates obtained in S13)−(the total number of the particulates with different sizes obtained in S13)*(the correct coefficient obtained in S12); and S15: obtaining the number of small-size particulates actually existing in the measured air flow according to the total number of the particulates with different sizes obtained in S13 and the number of the large-size particulates actually existing in the measured air flow obtained in S14, wherein the number of the small-size particulates actually existing in the measured air flow is calculated by the following formula:

(the total number of the particulates with different sizes obtained in S13)−(the number of the large-size particulates actually existing in the measured air flow obtained in S14).

3. The method according to claim 1, wherein the small-size particulates collected in Step S11 are generated by a standard particle generator, and/or are generated by burning a cigarette.

4. The method according to claim 3, wherein the total number of the particulates with different sizes is equal to the total number of the small-size particulates, and the number of the large-size particulates is the number of the misjudged small-size particulates of all the small-size particulates.

5. A method for simultaneously measuring mass concentrations of particulates with different sizes, comprising the following steps:
  S1: calculating a correction coefficient of the number of small-diameter particulates that are misjudged as large-diameter particulates; and
  SS2: correcting a measured number of small-diameter particulates or a measured number and mass concentration of large-diameter particulates according to the correction coefficient;
  wherein the large-diameter particulates are particulates with diameters greater than a maximum diameter of the small-diameter particulates;
  wherein calculating the correction coefficient of the number of the small-size particulates that are misjudged as the large-size particulates in Step S1 comprises the following steps:
  S21: collecting a measured air flow only containing small-size particulates, and detecting the number of particulates in the measured air flow to obtain a detection result; and
  S22: obtaining the proportion of small-size particulates that are misjudged as particulates with sizes greater than a maximum size of the small-size particulates and smaller than or equal to a maximum size of the large-size particulates according to the detection result, wherein the proportion is the correction coefficient of the number of the small-size particulates that are misjudged as the large-size particulates.

6. The method according to claim 5, wherein correcting the measured number and mass concentration of the large-size particulates according to the correction coefficient in Step S2 comprises the following steps:

S23: detecting, by a standard air quality detection device, the mass concentration of the small-size particulates in the measured air flow, and obtaining a first correlation coefficient between the number and mass concentration of the small-size particulates according to the number of the small-size particulates detected in Step S21;
  S24: obtaining a second correlation coefficient between the number and mass concentration of the particulates with the sizes greater than the maximum size of the small-size particulates and smaller than or equal to the maximum size of the large-size particulates according to the maximum size of the small-size particulates, the first correlation coefficient and the maximum size of the large-size particulates; and
  S25: calibrating the multi-channel air quality detection device according to the correction coefficient of the number of the small-size particulates that are misjudged as the large-size particulates, the first correlation coefficient and the second correlation coefficient, and calculating and correcting the measured mass concentration of the large-size particulates to obtain a corrected mass concentration of the large-size particulates.

7. The method according to claim 6, wherein in Step S23, the first correlation coefficient between the number and mass concentration of the small-size particulates is calculated by the following formula:

(the mass concentration of the small-size particulates in the measured air flow detected by the standard air quality detection device)/(the number of the small-size particulates).

8. The method according to claim 7, wherein in Step S24, the second correlation coefficient between the number and mass concentration of the particulates with the sizes greater than the maximum size of the small-size particulates and smaller than or equal to the maximum size of the large-size particulates is calculated by the following formula:

(the first correlation coefficient)*((the maximum size of the large-size particulates)/(the maximum size of the small-size particulates))$^3$.

9. The method according to claim 7, wherein in Step S25, the mass concentration of the large-size particulates is calculated by the following formula:

(the second correlation coefficient)*((the measured number of the large-size particulates)−(the number of the small-size particulates)*(the correction coefficient of the number of the small-size particulates that are misjudged as the large-size particulates))+(the calibrated mass concentration of the small-size particulates).

10. The method according to claim 5, wherein in Step S21, the number of the particulates in the measured air flow is detected through the following steps: detecting the measured air flow by a multi-channel particulate detection device, recording peak values of voltage pulses output by a photoelectric sensor in the multi-channel particulate detection device, taking a maximum peak value of a certain proportion of voltage pulses as a voltage threshold of particulates within a corresponding size range to obtain a voltage threshold of the small-size particulates and a voltage threshold of the large-size particulates, wherein particulates with pulse peak values smaller than or equal to the voltage threshold of the small-size particulates are judged as small-size particulates, and particulates with pulse peak values greater than the voltage threshold of the small-size particulates and smaller than or equal to the voltage threshold of the large-size particulates are judged as large-size particulates.

11. The method according to claim 5, wherein in Step S22, the correction coefficient of the number of the small-size particulates that are misjudged as the large-size particulates is calculated by the following formula:

(the number of the particulates with the sizes greater than the maximum size of the small-size particulates and smaller than or equal to the maximum size of the large-diameter particulates)/(the number of the small-size particulates).

12. The method according to claim 5, wherein the small-size particulates in Step S21 are generated by a standard particle generator, and/or are generated by burning a cigarette.

13. A device for simultaneously measuring mass concentrations of particulates with different sizes, comprising a photoelectric sensor and a calibration module, wherein the calibration module is configured to perform a method for simultaneously measuring mass concentrations of particulates with different sizes, the method comprising the following steps:
S1: calculating a correction coefficient of the number of small-size particulates that are misjudged as large-size particulates; and
S2: correcting a measured number of small-size particulates or a measured number and mass concentration of large-size particulates according to the correction coefficient;
wherein the large-size particulates are particulates with sizes greater than a maximum size of the small-size particulates; and
wherein calculating the correction coefficient of the number of the small-size particulates that are misjudged as the large-size particulates in Step S1 comprises the following steps:
S11: collecting a measured air flow only containing small-size particulates, and detecting, by a multi-channel air quality detection device, the number of particulates with different sizes in the measured air flow to obtain the total number of the particulates with different sizes and the number of large-size particulates; and
S12: dividing the number of the large-size particulates by the total number of the particulates with different sizes to obtain the correction coefficient of the number of the small-size particulates that are misjudged as the large-size particulates.

14. The device according to claim 13, wherein correcting the measured number of the small-size particulates according to the correction coefficient in Step S2 comprises the following steps:
S13: detecting, by the multi-channel air quality detection device, the number of particulates with different sizes in the measured air flow to obtain the total number of the particulates with different sizes and the number of large-size particulates;
S14: correcting the number of large-size particulates actually existing in the measured air flow according to the correction coefficient of the number of the small-size particulates that are misjudged as the large-size particulates obtained in S12, as well as the total number of the particulates with different sizes and the number of the large-size particulates obtained in S13, wherein the number of the large-size particulates actually existing in the measured air flow is calculated by the following formula:

(the number of the large-size particulates obtained in S13)−(the total number of the particulates with different sizes obtained in S13)*(the correct coefficient obtained in S12);

and
S15: obtaining the number of small-size particulates actually existing in the measured air flow according to the total number of the particulates with different sizes obtained in S13 and the number of the large-size particulates actually existing in the measured air flow obtained in S14, wherein the number of the small-size particulates actually existing in the measured air flow is calculated by the following formula:

(the total number of the particulates with different sizes obtained in S13)−(the number of the large-size particulates actually existing in the measured air flow obtained in S14).

15. The device according to claim 13, wherein the small-size particulates collected in Step S11 are generated by a standard particle generator, and/or are generated by burning a cigarette.

16. The device according to claim 15, wherein the total number of the particulates with different sizes is equal to the total number of the small-size particulates, and the number of the large-size particulates is the number of the misjudged small-size particulates of all the small-size particulates.

* * * * *